United States Patent [19]

Norton et al.

[11] Patent Number: 4,531,933
[45] Date of Patent: Jul. 30, 1985

[54] HELICAL URETERAL STENT

[75] Inventors: William J. Norton, Berkeley Heights; Irwin S. Wolosky, Parsippany, both of N.J.

[73] Assignee: C. R. Bard, Inc., Murray Hill, N.J.

[21] Appl. No.: 447,679

[22] Filed: Dec. 7, 1982

[51] Int. Cl.³ .............................................. A61M 25/00
[52] U.S. Cl. .......................................... 604/8; 604/281
[58] Field of Search ................... 604/8, 264, 280, 281, 604/55, 104, 268; 128/130, 127

[56] References Cited

U.S. PATENT DOCUMENTS 3,811,423  5/1974  Dickinson, III et al. ............. 604/55
3,920,023  11/1975 Dye et al. ............................ 604/281
4,212,304  7/1980  Finney ................................. 604/170
4,307,723  12/1981 Finney ................................. 604/8
4,365,632  12/1982 Kortum ............................... 128/130

Primary Examiner—C. Fred Rosenbaum
Assistant Examiner—Michelle N. Lester
Attorney, Agent, or Firm—Dennison, Meserole, Pollack & Scheiner

[57] ABSTRACT

A ureteral stent for maintaining drainage of urine between the kidney and the bladder including an elongated flexible silicone tubular member having a series of helical coils on its distal end, the longitudinal axis of which is parallel to the tubular member. A retention coil is formed on the proximal end of the tubular member for reception in the renal pelvis and drainage holes are formed along the length of the stent. The stent is straightened for insertion by means of a wire guide.

7 Claims, 6 Drawing Figures

HELICAL URETERAL STENT

BACKGROUND AND PRIOR ART

The general field of this invention is directed to the art of urology for achieving and maintaining internal ureteral drainage in a variety of pathologic conditions. Frequently, intubation of a ureteral stent is necessary with patients having malignant diseases, progressive azotemia and ureteral obstructions. Such obstructions are frequently caused by carcinoma of the prostate, bladder, cervix, uterus, ovary and rectosigmoid. Generally such stents are utilized on a temporary basis and are only left indwelling until a surgical procedure can be performed. Some stents on the other hand may be utilized as a permanent method of diversion and often for palliation and relief of pain.

The use of stenting catheters has been substantiated in the medical literature and in general practice. Note for example, Gibbons, R. F., Correaa, R. J., Jr., Cummings, K. B. and Mason, J. T.: "EXPERIENCE WITH INDWELLING URETERAL STENT CATHETERS" *Journal of Urology,* 1976 115:22 and Hepperten, Thomas W., M. D.: "SELF-RETAINED INTERNAL URETERAL STENTS: A NEW APPROACH". *The Journal of Urology* June 1978 119:731–734.

Indwelling ureteral stents also aid ureteral alignment and maintenance of ureteral caliber. The devices can be placed either endoscopically or utilizing open surgery to provide drainage of the kidney to the bladder when the anatomical ureter cannot adequately perform this task by itself.

Ureteral stents are shown in the prior art and emphasis in recent years has been directed to providing means associated with the stents to prevent upward or downward migration. Note for example, the patent of Gibbons, U.S. Pat. No. 3,938,529, which utilizes flexible, laterally extending barbs for this purpose. Barbs of this type, however, increase the diameter of the stent and make it more difficult to insert and in some instances can cause the stent to migrate outside the bladder creating problems for the physician. Finney, U.S. Pat. No. 4,212,304, provides a ureteral stent having opposed hook-shaped elements for retention. Devices of this type must be provided in numerous lengths to accommodate the particular patient. Additionally, note the ureteral prosthesis of Rey et al, U.S. Pat. No. 4,225,979.

SUMMARY AND OBJECTS OF THE INVENTION

We have provided a new helical coil stent which is simple in construction, relatively easy to insert cystoscopically and is safe for use by the patient. Additionally, the unique design of our new helical coil stent provides an effective means for preventing upward or downward migration of the device and yet provides a non-traumatic spring effect when the patient is active.

The new stent need only be provided in one length for each French size (diameter). It is the helical coil configuration on the distal or bladder end of the stent which makes the single size feature possible and eliminates the necessity for radiographic sizing prior to insertion and the inconvenience of inadvertently placing a stent that may either be too long or too short as is prevalent with the prior art devices.

It is an object of our invention to provide a new ureteral stent having a novel retention means on at least one end thereof.

Another object of the invention is to provide a novel helical ureteral stent that is simple to insert and need only be provided in a single length to eliminate the need for radiographic sizing.

Another object of our invention is the provision of a new coil stent which is relatively inexpensive, safe and efficient in use and which may be inserted utilizing conventional techniques.

Further objects and advantages will become apparent from a consideration of the following drawings and detailed description.

DETAILED DESCRIPTION

Figure 1:
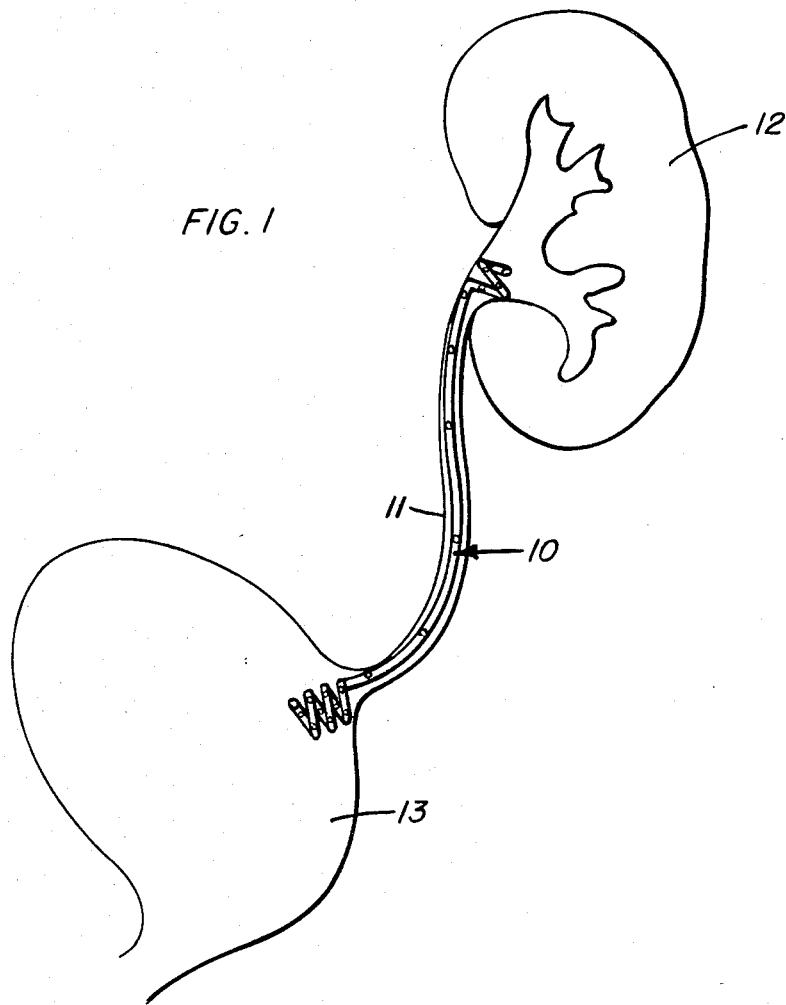
FIG. 1 is a schematic isometric view illustrating the ureteral stent in position between the kindney and the bladder.

Our new ureteral stent is shown generally in FIG. 1 at 10. It is depicted in place within the affected ureter 11 which connects between the renal pelvis 12 and the bladder 13. For the purpose of further description, and utilizing conventional medical terminology, the end of the stent received in the kidney will be designated as the proximal end and the opposite end of the stent received in the bladder will be termed the distal end.

While the stent may be formed of any bio-compatible material, a soft, flexible, medical grade silicone plastic is preferred. This material resists tissue adherence and encrustation. The material is also chosen to be radioopaque in order to facilitate insertion. The stent may be formed with different outside diameters, as for example French sizes 6, 7 and 8, however, it is only necessary to provide a single length for all uses and a length of 31 centimeters has been found ideal for this purpose. In the preferred form of the invention shown in FIG. 2, the proximal end of the stent is provided with a relatively short helical coil configuration 14, shown for example as having only one and a half revolutions. At the distal end, the stent is set with a longer coil 15 which in the embodiment shown represent five coils. It will be seen that the longitudinal axis of the helical construction is parallel to the main body 16 of the stent but offset therefrom in the preferred embodiment.

Figure 2:
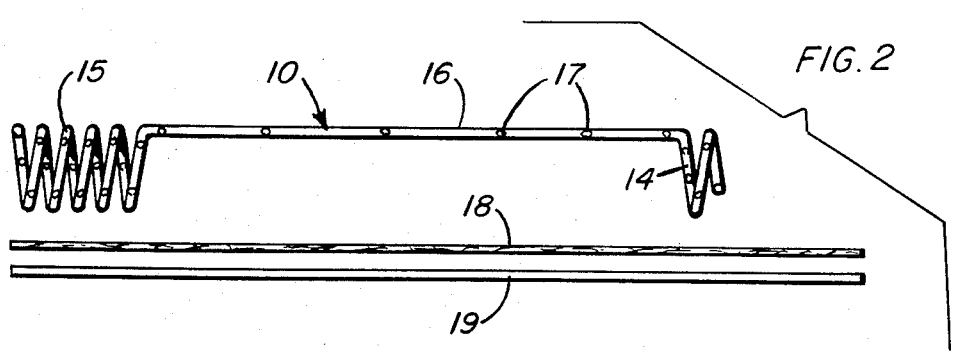
FIG. 2 is a front elevation of our new ureteral stent and also including the means used for inserting the same.
Figure 3:
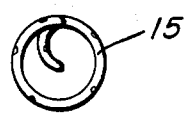
FIG. 3 is an end view taken from the left of FIG. 2 of the stent only.

Drainage holes 17 are provided throughout the entire length of the helical coil stent leading to the lumen, although there is a greater concentration of the drainage holes at the proximal end. When the stent is formed, both ends may be closed off, although it will be seen later herein that during insertion the distal end is clipped off to permit use of the spring wire guide and push catheter. The spring wire guide used for insertion is shown in FIG. 2 at 18 and the plastic push catheter at 19.

Figure 4:
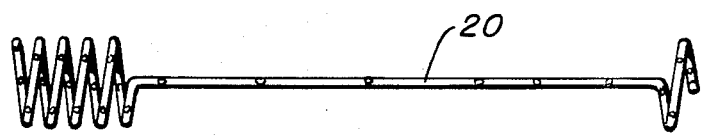
FIG. 4 is an elevation of a first modified form of the ureteral stent.

In the modified form of stent shown in FIG. 4, it will be noted that the coils are formed with the helical axis concentric with the main tubular body 20 of the stent.

Figure 5:
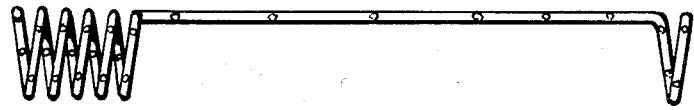
FIG. 5 is an elevation of a second modified form of ureteral stent.

The FIG. 5 embodiment is basically the same as the preferred embodiment, however, here the proximal end coils are formed with a constant radius wherein the preferred form is spiralled.

Figure 6:
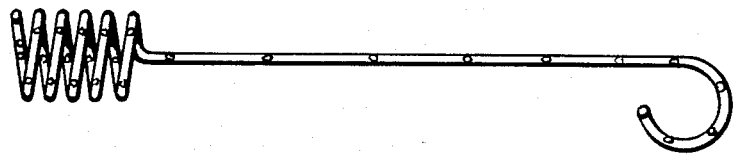
FIG. 6 is an elevation of a further modified form of the invention having a hook-shaped retaining means.

The form of the invention shown in FIG. 6 utilizes the coaxial coil arrangement of FIG. 4 on the distal end, however, the proximal end is formed with a "J hook" 21 instead of the helical coil.

It will be appreciated that with each of the designs, the retention coils or hook forms provide an effective means for preventing both upward or downward migration of the stent yet the construction is soft and pliable and provides a non-traumatic "spring effect" especially during times when the patient is active.

The technique for selection and insertion of our new ureteral stent is conventional. The surgeon selects the proper French size, as one would normally do with any ureteral catheter. The stent of the present invention is designed to accommodate ureteral lengths of from 11 centimeters to 30 centimeters. At full extension of the stent, at least one coil on the distal end of the stent must remain in the bladder to prevent upward migration.

When placing the stent using endoscopic means, the distal end is clipped off as noted previously. The spring wire guide 18 is inserted through the clipped end of the stent lumen and the stent is threaded over the wire. This serves to straighten the retention coils of the helix. Care must be taken not to force the wire guide through the proximal end of the stent. Subsequently, the plastic push catheter is slipped on next and this serves to hold the stent in position when the wire guide is withdrawn from the stent after insertion and placement.

The assembly is inserted as a conventional ureteral catheter. Once the renal pelvis has been entered, confirmation can be obtained by a radiograph. Thereafter the spring wire guide is gently withdrawn while holding the plastic push catheter in position. After the wire guide 18 and the push catheter 19 have been completely withdrawn, the stent is left in place and any excess stent coils in the bladder may be clipped and removed endoscopically if desired. The surgeon must insure, however, that at least one retention coil is left in the bladder for the purpose of precluding upward migration of the stent.

Our new stent may also be inserted into the ureter during open surgery. In this application, the distal end tip is not clipped off and the plastic push catheter 19 is not necessary. The spring wire guide 18, however, is inserted into the stent via one of the side drainage holes 17. The coil is straightened and the stent is advanced into the ureter via a surgical incision. If the bladder end is inserted first, the physician can determine when the stent is in the bladder by aspirating urine with syringe suction on the stent at the drainage hole closest to the ureteral entry point. Placement of the stent into the renal pelvis is accomplished by using the same technique. Whether or not the stent is removed is of course left to the discretion of the physician. Our stent may be removed endoscopically utilizing forceps.

Various modifications can be made in the constructions noted above without departing from the invention as claimed. For example, if desired, means for increasing the rigidity of the proximal and distal coils may be incorporated. To this extent, fabric, metal or plastic materials may be incorporated into the coils for the purpose of making them more rigid and therefore more resistant to migration. Further, measurement markings or indexes may be painted or otherwise applied to the stent which would be visible during X-ray.

We claim:

1. An adjustable length ureteral stent for maintaining drainage between the kidney and bladder consisting essentially of an elongated flexible tubular member provided with drainage means extending along the length thereof, retention means on the proximal end of the tubular member adapted to be received in the kidney, a plurality of helical coils formed on the distal end of the tubular member, at least one of which is adapted in use to remain in the bladder, the remaining coils being adapted to straighten out as an extension of the tubular member to provide length adjustment to accommodate said stent to different patient sizes, the central axis of the helix of the coils being substantially parallel to the portion of the tubular body between the coils and the proximal end retention means.

2. A ureteral stent as defined in claim 1 wherein the tubular member has an internal lumen and the drainage means consists of a plurality of holes extending into the lumen.

3. A ureteral stent as defined in claim 2 wherein the drainage holes extend along the entire stent with a greater concentration thereof adjacent the proximal end thereof.

4. A ureteral stent as defined in claim 1, wherein the retention means on the proximal end consists of at least one helical coil substantially coaxial with the coils on said distal end 5. A ureteral stent as defined in claim 4, wherein the axis of the helix of the coils is offset from the portion of the tubular body between the coils and the proximal end retention means.

6. A ureteral stent as defined in claim 4, wherein the axis of the helix of the coils is coaxial with the portion of the tubular body between the coils and the proximal end retention means.

7. A ureteral stent as defined in claim 1, wherein the retention means comprises a hook formation extending less than 360°.

* * * * *